United States Patent [19]

Chin

[11] Patent Number: 5,591,183
[45] Date of Patent: Jan. 7, 1997

[54] DISSECTION APPARATUS

[75] Inventor: Albert K. Chin, Palo Alto, Calif.

[73] Assignee: Origin Medsystems, Inc., Menlo Park, Calif.

[21] Appl. No.: 421,481

[22] Filed: Apr. 12, 1995

[51] Int. Cl.⁶ .................................................. A61B 17/22
[52] U.S. Cl. ........................... 606/159; 606/167; 606/170
[58] Field of Search ..................................... 606/170, 167, 606/159–161

[56] References Cited

U.S. PATENT DOCUMENTS

| | | |
|---|---|---|
| 207,932 | 9/1878 | Alvord . |
| 3,224,320 | 12/1965 | Knudsen . |
| 3,437,747 | 4/1969 | Sheldon . |
| 3,556,085 | 1/1971 | Takahashi . |
| 3,821,956 | 7/1974 | Gordhamer . |
| 4,319,563 | 3/1982 | Kubota . |
| 5,122,152 | 6/1992 | Moll . |
| 5,159,920 | 11/1992 | Condon et al. . |
| 5,163,949 | 11/1992 | Bonutti . |
| 5,271,380 | 12/1993 | Riek et al. . |
| 5,314,440 | 5/1994 | Shapiro . |
| 5,331,975 | 7/1994 | Bonutti . |
| 5,346,503 | 9/1994 | Chow . |
| 5,373,840 | 12/1994 | Knighton . |
| 5,385,572 | 1/1995 | Nobles et al. . |
| 5,397,333 | 3/1995 | Knoepfler . |
| 5,423,842 | 6/1995 | Michelson . |
| 5,429,117 | 6/1995 | McNamara et al. . |

FOREIGN PATENT DOCUMENTS

| | | |
|---|---|---|
| 0312787A1 | 4/1989 | European Pat. Off. . |
| 0347140A1 | 12/1989 | European Pat. Off. . |
| 0369937A1 | 5/1990 | European Pat. Off. . |
| 0369936A1 | 5/1990 | European Pat. Off. . |
| 0642764A1 | 3/1995 | European Pat. Off. . |
| 1370580 | 12/1964 | France . |
| 2218901 | 10/1973 | Germany . |
| 2538738 | 3/1976 | Germany . |
| 2922239 | 12/1990 | Germany . |

OTHER PUBLICATIONS

"Selected Applications of Balloon Dissection", Thomas J. Fogarty, J. Stephen Scott, Roger de la Torre, Bela S. Denes, George D. Hermann, Surgical Technology International III, International Developments in Surgery and Surgical Research, 1994, pp. 45–52.

"Extraperitoneal Laparoscopic Hernia Repair: Experience In 178 Patients", Barry N. Gardiner, Albert K. Chin, Frederic M. Moll, Zoltán Szabó, Surgical Technology International III, International Developments in Surgery and Surgical Research, 1994, pp. 237–242.

Primary Examiner—Corrine M. McDermott
Assistant Examiner—Perry E. Van Over
Attorney, Agent, or Firm—Albert C. Smith

[57] ABSTRACT

The present invention provides a multiple cannula assembly which includes an inner cannula having a first balloon for making an elongated cavity by progressive dissection, an endoscope for visually monitoring the dissection, and an outer cannula having a second balloon for enlarging the elongated cavity. The inner cannula is independently movable from the outer cannula and is reversibly extendible beyond the distal end of the outer cannula. The present invention also includes a method of using such a cannula assembly for dissecting an elongated cavity along the course of a small blood vessel and subsequently harvesting the blood vessel.

6 Claims, 4 Drawing Sheets

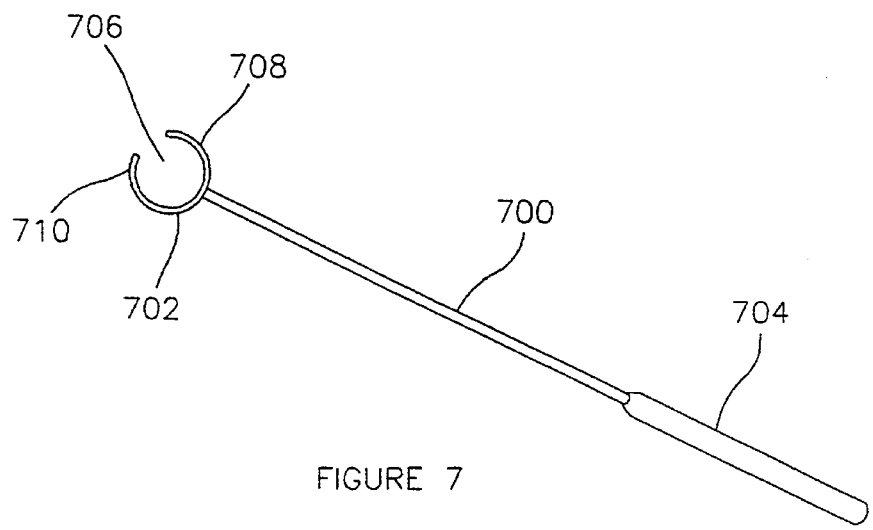
FIGURE 7
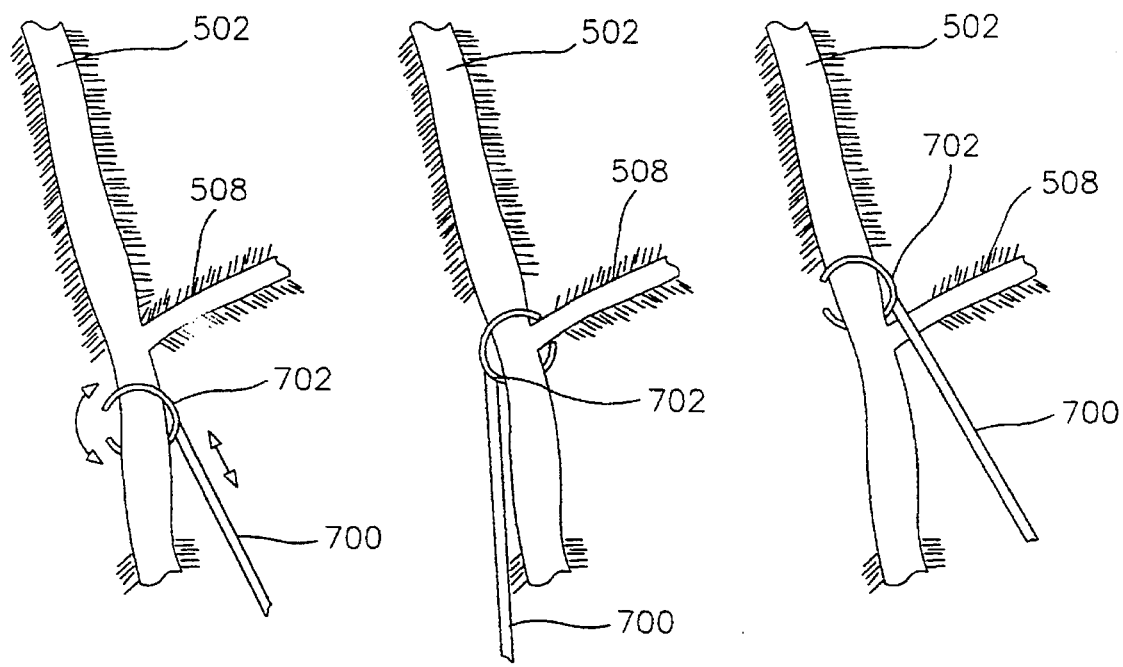
FIGURE 8A
FIGURE 8B
FIGURE 8C

DISSECTION APPARATUS

BACKGROUND OF THE INVENTION

1. Related Application

The subject matter of this application is related to the subject matter of U.S. patent application Ser. No. 08//269, 666, now abandoned, entitled "EVERYTHING CANNULA APPARATUS AND METHOD" filed on Jul. 1, 1994 by Albert K. Chin. The above application having the same assignee as the present invention and is incorporated herein by reference in its entirety.

2. Field of the Invention

The present invention relates generally to a dissection cannula assembly used for forming an elongated cavity in tissue planes particularly along the course of a small blood vessel. The present invention relates specifically to an assembly having multiple cannulae and balloons.

3. Description of Background Art

Present methods for the formation of an elongated cavity involve the use of blunt probes that are pushed through body tissue to accomplish the dissection. The force exerted by the passage of mechanical probes may lead to blood vessel avulsion and trauma to tissue and internal organs.

The problem becomes acute when dissecting and harvesting blood vessels having a small diameter of about 3 to 8 mm. The techniques which are used for dissection of larger blood vessels such as the aorta are not applicable. The aorta is located in the retroperitoneum, bounded by the peritoneum on one side and the psoas muscle on the other side. An everting balloon placed in the infrarenal space located just below the kidney will track easily down the length of the aorta along a natural cleavage plane when inflated.

An everting type of balloon experiences difficulty in dissection when applied to smaller diameter vessels. This is due to the greater adhesion that exists between small diameter blood vessels and the tissue that surrounds these vessels, as compared with the aorta and the tissue that surrounds the aorta. For example, if an everting balloon is placed adjacent to the saphenous vein in the leg, it usually squirts off in either direction upon inflation rather than track along the vein. This is due to the greater adhesion between the saphenous vein and the muscle that surrounds the vein.

Several balloon catheters are disclosed in various issued patents and publications. Exemplary everting balloon catheters used for arterial dilation include U.S. Pat. No. 4,479,497 (Fogarty et al., Oct. 30, 1984), U.S. Pat. No. 4,863,440 (Chin, Sep. 5, 1989), U.S. Pat. No. 4,696,304 (Chin, Nov. 29, 1987), and U.S. Pat. No. 4,630,609 (Chin, Dec. 23, 1986).

Double lumen everting balloon catheters, such as those disclosed in the Fogarty et al. '497 and the Chin '440 patents, have a through-lumen that permits the passage of an endoscope. However, an endoscope used in conjunction with those disclosed catheters in unable to monitor the dissection process, since the endoscope lies within the central lumen proximal to the everting balloon. As the balloon everts from the catheter, the internal inflation pressure squeezes the walls of the balloon and closes off the distal viewing channel. Also, the area that requires monitoring during balloon dissection is located at the advancing front of the everting balloon. This area corresponds to the balloon/tissue interface subject to forces that cause tissue separation. Thus, an endoscope in the central lumen of existing double lumen everting balloon catheters is unable to view the tissue separation area, since a double layer of balloon membrane lies between the endoscope and the tissue blocking the endoscopic line of sight. This double layer obscures and distorts the viewing image.

The catheter disclosed in the Chin '304 patent includes an outer catheter and an inner catheter slidably mounted within the outer catheter lumen. The inner catheter is provided with an inflatable balloon which is used to occlude an artery and it makes a pressure measurement through a separate lumen. The inner catheter is advanced through the outer catheter until the inflated balloon occludes the artery.

The dilatation catheter disclosed in the Chin '609 patent includes a double balloon system at the distal end of the catheter. The more distal of the two balloon elements is an everting type. In close proximity is a second balloon element of the sleeve type. By the eversion action of the distal inverted balloon, the catheter works its way into a stenosis zone with a minimum tendency to dislodge plaque and form an embolus. The proximal sleeve balloon is inflated to prevent the catheter from backing out of the artery upon eversion of the distal balloon through a fight stenosis.

Other versions of balloon dissection cannulae are commercially available, for example, from Origin Medsystems, Inc., the assignee herein. One such version uses a spherical, elastomeric balloon, and another such version uses a generally elliptical, inelastic balloon that is rolled up outside the lumen. These cannulae dissect generally spherical cavities.

SUMMARY OF THE INVENTION

The present invention provides a cannula assembly for dissecting an elongated cavity in tissue particularly along the course of a vessel. The assembly includes an outer cannula having a plurality of lumens substantially extending the length thereof. The outer cannula has a proximal closed end and a distal blunt end. An inner cannula is slidably disposed in a first one of the lumens and has a first balloon capable of being inflated in response to fluid under pressure applied thereto. The inner cannula is positioned at a predetermined location within an initial dissection to progressively dissect the elongated cavity along the course of the vessel distal to the outer cannula. The assembly also includes a second balloon having proximal and distal end portions attached to the outer cannula at the distal end portion thereof. The second balloon is capable of being radially and reversibly expandable in response to fluid under pressure applied thereto. The second balloon enlarges the diameter of the elongated cavity. A second one of the lumens is disposed to receive an endoscope therein. The endoscope visualizes the progressive dissection of the elongated cavity along the course of the vessel.

Specifically, the cannula assembly of the present invention includes multiple cannulae, preferably two cannulae, with an elastomeric or a nonelastomeric balloon attached to the distal end of both of the cannulae. Upon repetitive and successive inflation of each balloon an elongated cavity is progressively dissected. At least one of the cannulae includes a plurality of lumens. An endoscope may then be extended from one of the lumens to monitor the progress of the dissection.

A method also is disclosed for dissection of an elongated cavity particularly along the course of a vessel using a cannula assembly. The method includes the steps of: bluntly dissecting an initial cavity; advancing the inner cannula along the cavity; inflating and deflating the first balloon within the cavity to elongate the cavity along the course of the vessel; repeating the prior steps of advancing the inner cannula and inflating and deflating the first balloon to continue the dissection until the cavity is sufficiently elongated to advance the outer cannula therein; advancing the outer cannula within the elongated cavity; and, inflating and deflating the second balloon of the outer cannula within the elongated cavity to enlarge the diameter of the elongated cavity. The method further may include removing the cannula assembly, then maintaining the elongated cavity using insufflated gas through a balloon cannula that seals the incision against gas leakage, a structural balloon, or a mechanical structural support.

The present invention also contemplates providing a dissection device for isolating a vessel partially exposed by an elongated cavity along the course of the vessel. The device includes an open rigid ring having at least one cutting edge capable of dissecting tissue. The cutting edge extends substantially along the circumference of the ring. The ring has an opening through the body of the ring. The opening has a width equal or slightly larger than the width of the vessel. An elongated, rigid handle connects and extends generally perpendicular to the body of the ring. If the isolated vessel is the saphenous vein, it may be harvested and removed for use as a coronary artery or vascular graft, or it may be left in place as an in-sire femorapopliteal or femoral-distal graft. The side branches of the vein are ligated, clipped, or occluded in both applications.

BRIEF DESCRIPTION OF THE DRAWINGS

FIG. 7 is a perspective view of a dissection instrument of the present invention for performing the inventive methods herein; and FIGS. 8A–C are longitudinal cross-sectional views of the vessel enlarged in FIG. 5 demonstrating the use of the inventive dissection instrument.

DETAILED DESCRIPTION OF THE PREFERRED EMBODIMENTS

In accordance with one embodiment of the present invention, a cannula assembly includes an inner cannula having a first balloon for making an elongated cavity by progressive dissection, an endoscope for visually monitoring the dissection, and an outer cannula having a second balloon for enlarging the elongated cavity. The present invention also includes a method of using such a cannula assembly for dissecting an elongated cavity along the course of a small blood vessel and subsequently harvesting the blood vessel, or using the blood vessel as an in-situ graft.

Figure 1:
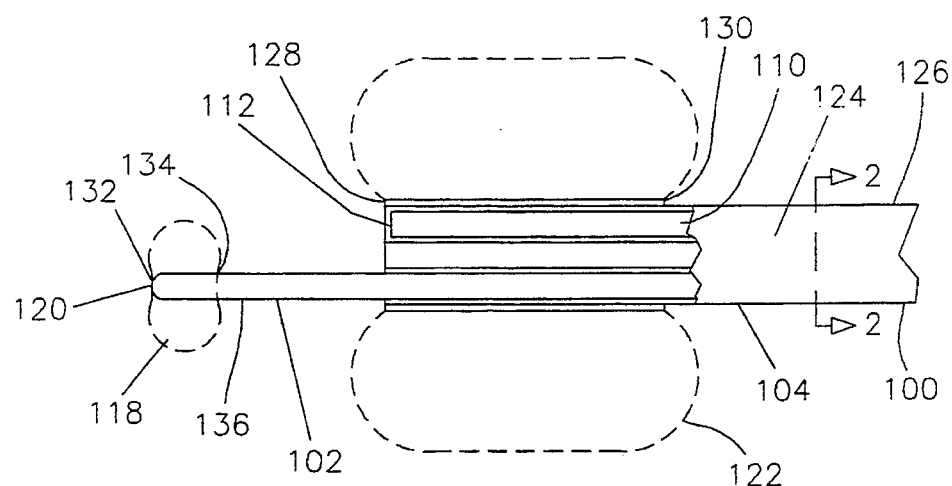
FIG. 1 is a partial side view of a cannula assembly of the present invention with the outer and inner cannula partially cut away to illustrate the lumens therein.

FIG. 1 shows an embodiment of the cannula assembly 100 of the present invention. The assembly 100 includes an inner cannula 102 having a smaller diameter than an outer cannula 104. Preferably, the diameter of the inner cannula 102 is about 1.5 mm and the diameter of the outer cannula is about 5 min. The inner cannula 102 is independently movable from the outer cannula 104 and is reversibly extendible beyond the distal end 112 of the outer cannula.

Figure 2:
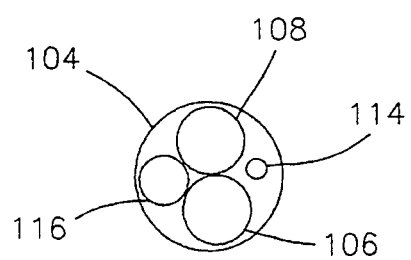
FIG. 2 is a cross sectional view of the inventive cannula assembly along the lines 2—2 in FIG. 1 isolating the lumens therein.

The outer cannula 104 contains a plurality of lumens as illustrated in FIG. 2 which substantially extend the length of the outer cannula. One lumen 106 slidably retains the inner cannula 102. Another lumen 108 accommodates a fiberoptic endoscope 110 which views out from the distal end 112 of the outer cannula. Another lumen 114 is used to supply pressurized fluid, such as a gas or liquid, to the distal end 112 of the outer cannula. The remaining lumen 116 may be used for irrigation and aspiration.

Referring to FIG. 1, the inner cannula 102 includes a first balloon 118 located at the distal end 120 of the inner cannula 102. The first balloon 118 is preferably a coaxial, sleeve type balloon having sufficient columnar strength to dissect planes of tissue. The first balloon 118 is about 7 mm in length and inflates to an outer diameter of approximately 7 mm. The first balloon 118 may be elastic or inelastic. The distal end 132 of the first balloon 118 is attached to the outer edges of the distal end 120 of the inner cannula to ensure that the first balloon 118, when in its inflated state (shown in phantom in FIG. 1), extends outwardly from the distal end 120 of the inner cannula and completely encloses that end of the inner cannula 102. The proximal end 134 of the first balloon is attached to the exterior wall 136 of the inner cannula. In its deflated state, the inner cannula 102 may be introduced into the dissection site. The inflation of the first balloon 118 is provided by connection to a lumen 126 which provides a pressurized fluid through the inner cannula 102.

The outer cannula 104 includes a second balloon 122 which is attached near the distal end 112 on the exterior wall 124 of the outer cannula. The second balloon 122 may be elastic or inelastic, although an elastomeric balloon is preferred because it achieves a smaller, smoother outer profile. Fully inflated, the diameter of the second balloon 122 is about 3 cm. Preferably, a sleeve type of balloon is used as the second balloon 122 wherein both the distal end 128 and proximal end 130 of the second balloon are secured to the exterior wall 124 of the outer cannula. The inflation of the second balloon 122 is provided by connection to the lumen 114 which provides a pressurized fluid through the outer cannula 104.

The present invention is illustrated using a sleeve type of balloon with the inner and outer cannulae 102, 104. Other balloon types are suitable for use with the present invention such as, and not limited to, using an invertable balloon positioned by a separate lumen in either the inner or outer cannula, or both. Other balloon types which have sufficient columnar strength to dissect planes of tissue are suitable for use as the first balloon 118.

The inner and outer cannulae 102, 104 may be manufactured from a variety of bioinert, substantially inelastic materials. Preferred materials include polyethylene, polyurethane, polyvinyl chloride, polyimide plastic, and the like preferably material having a tensile strength of at least 10,000 psi. Preferably, each lumen of the outer cannula 104 has a wall thickness of between about 0.001 inch and 0.003 inch.

The fiberoptic endoscope 110 also has an outer diameter of approximately 1.5 mmm. The fiberoptic endoscope may be permanently built into the outer cannula 104, or it may be a separate device that is advanced through the endoscope lumen 108. The endoscope 110 is positioned within the lumen 108 such that the endoscope tip lies in correct position to allow unimpeded visualization of the vessel outside of the outer cannula 104 while the inner cannula 102 translates axially with respect to the outer cannula 104, telescoping out of the distal end 112 of the outer cannula. Providing a separate lumen 108 for the endoscope 110 permits the endoscope 110 to be advanced beyond the distal end 112 of the outer cannula 104 when the first balloon 118 is in its partially inflated state for more clear viewing of the first balloon 118 and the surrounding tissue. A preferred endoscope 110 having a tubular diameter of about 1.7 mm is commercially available from Origin Medsystems, Inc. of Menlo Park, Calif. However, other commercially available endoscopes 110 that may be used in practicing the present invention include those which are as small as 1.00 to 1.75 mm in diameter.

Figure 3:
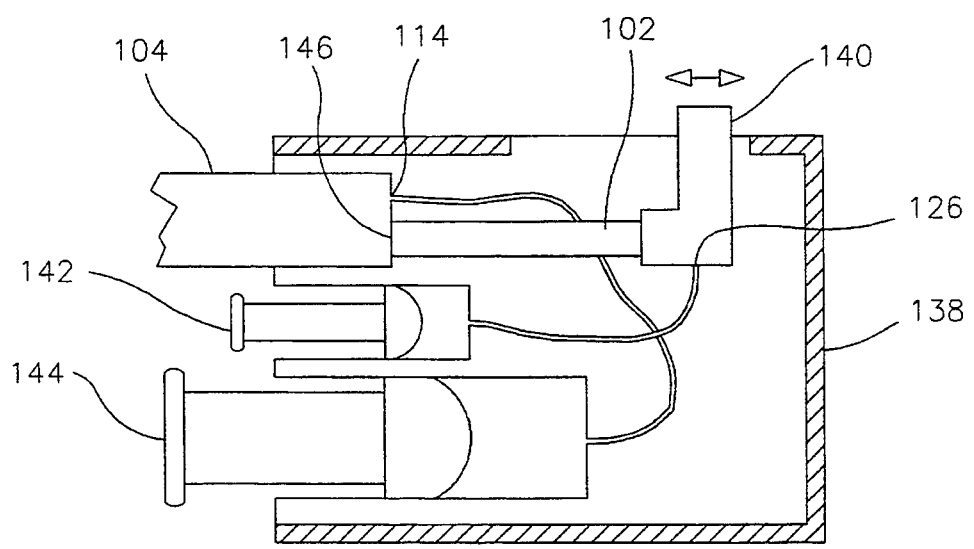
FIG. 3 is a partial side view of a cannula assembly of the present invention with the proximal end of the assembly cut away.

One embodiment of the proximal end 138 of the outer cannula 104 is depicted in FIG. 3. A slide control 140 is used to reversibly extend the inner cannula 102 out of the lumen 106 beyond the distal end 122 of the outer cannula. An integral first plunger device 142, similar to a manually operated syringe, is connected at an inflation port to the lumen 126 in the inner cannula and is used to control the inflation of the first balloon 118. An integral second plunger device 144 is connected to the lumen 114 in the outer cannula and is used to control inflation of the second balloon 122. The proximal end 138 of the outer cannula preferably is sealed. In addition, a conventional sliding seal 146 is provided around the inner cannula 102 within the lumen 126.

Figure 4:
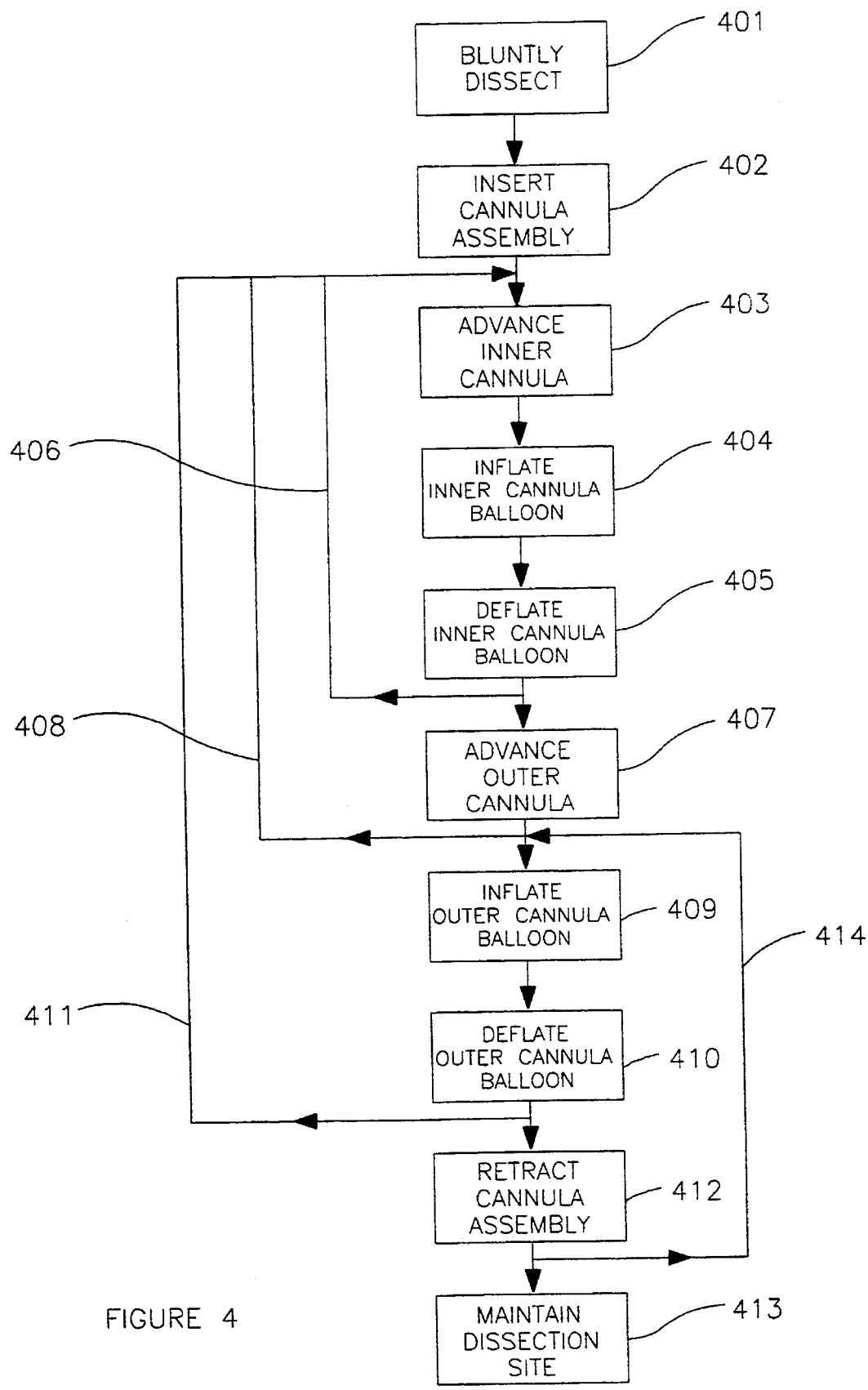
FIG. 4 is a flowchart of inventive methods of dissecting tissue using the cannula assembly of the present invention.

Methods for dissecting an elongated cavity using the cannula of the present invention is shown in the flow diagram of FIG. 4. Although the dissection of an elongated cavity along the course of a vessel is specifically described, the present invention is generally applicable for dissecting any tissue. The method includes the steps of incising the skin and bluntly dissecting 401 through the subcutaneous tissue to the level of the vessel. Dissection is performed to separate the vessel from adjacent tissue for a length of approximately 1 to 2 cm. The dissection may be performed with a pair of curved Metzenbaum scissors, using the tips of the scissors to cut and bluntly spread in a plane between the vessel and the adjacent tissue.

The cannula assembly 100 is advanced 402 into this dissected space with the inner cannula 102 retracted into the outer cannula 104. With the fiberoptic endoscope 110 visualizing down the course of the vessel, the inner cannula 102 is advanced forward 403, probing between the vessel and the adjacent tissue in the plane initiated by blunt dissection.

The small diameter first balloon 118 is inflated 404 to create a cavity of about 7 mm in diameter adjacent to the vessel. The first balloon 118 is then deflated 405. If the dissection along the course of the vessel is not sufficient to advance the outer cannula 104, the method returns 406 to the step of advancing the inner cannula 403 forward slightly and repeating the steps of inflating 404 and deflating 405 the first balloon 118 to continue the dissection along the course of the vessel.

When a cavity of about 1–2 cm in length has been formed by the inner cannula 102, the large diameter outer cannula 104 may be advanced 407 forward slightly into the 7 mm cavity. The method then returns 408 to probing and advancing 403 with the small diameter inner cannula 102.

The cannula assembly 100 provides atraumatic vessel dissection by using the inner cannula 102 under direct vision to bluntly probe between the vessel and its adjacent tissue, pre-dilating to allow the entrance of the larger outer cannula 104, which then achieves the full diameter dissection. The fiberoptic endoscope 110 is able to visualize the advancement of the inner cannula 102 and allow the surgeon to guide its positioning. Such visual control is prevented if a single balloon cannula is applied, since the endoscope resides in the tip of such a cannula, and the tip itself can not be viewed as it tracks through tissue. The use of the small diameter inner cannula 102 to precede the placement of the larger diameter outer cannula 104 results in safer dissection. The smaller diameter inner cannula 102 exerts a shear force over a smaller area on the vein and its adjacent tissue during advancement, as much less surface area is present in the profile of the smaller diameter inner cannula 102.

When sufficient length of the 7 mm cavity has been dissected to accommodate passage of several centimeters of the distal tip 112 of the outer cannula 104, the second balloon 122 on the large diameter cannula is inflated 409 to form a cavity of about 3 cm in diameter. The second balloon 122 is then deflated 410.

The method returns 411 to the step of advancing the inner cannula 403 and the steps of inflating 404 and deflating 405 the first balloon 118 as described above. Successive application of the inner and outer cannulae 102, 104 is used to form a cavity along the entire length of the vessel. Once the elongated cavity is complete, the method retracts 412 the cannula assembly 100 completely from the elongated cavity.

The method then maintains 413 the dissection site. Following use of the cannula assembly 100 to form an elongated cavity along the course of a vessel, the cavity must be supported to allow procedures to be performed on the vessel, such as vessel dissection, grating of the vessel, or vessel harvesting. A blunt tip trocar may be used to seal the entrance incision and allow gas insufflation to be used to maintain the cavity. One blunt tip balloon trocar suitable for use herein is presently marketed by Origin Medsystems, Inc. of Menlo Park, Calif.

Another method of maintaining the cavity is to make an incision at the distal extent of the dissected cavity and insert a double rod system through the cavity. The double rods are suspended via a laparoscopic mechanical lifting device to maintain the cavity. This system allows instruments to be advanced into the cavity via simple incisions, without the requirement for trocars with gas sealing valves, as is the case with gas insufflation.

Alternatively, an inflatable structural balloon or mechanical structure may be used to support the dissected cavity. For example, the cavity may be maintained by mechanical retraction or by a mechanical fan retractor attached to a powered lifting arm plus a separate flat balloon retractor used to displace the side wall of the cavity. The endoscope 110 may be introduced behind the legs of the fan retractor that connect to the mechanical lifting arm.

The vessel is completely dissected within the formed cavity, using laparoscopic instruments such as graspers, scissors, hooks, and blunt probes. Side branches to the vessel may be ligated using suture ties, clipped using titanium vessel clips, cauterized using electrocautery, or a combination of these. The dissected vessel is removed from the cavity and it may be used as a conduit for an arterial bypass procedure, or the vessel is left in place to be used as an in-situ bypass graft.

The present invention also contemplates an alternative method wherein the small diameter cavity, described above as about 7 mm, is formed along the entire length of the vessel before the cavity is then enlarged. As illustrated in FIG. 4, the steps of making a blunt dissection 401, inserting 402 the cannula assembly 100 and successively advancing 403 the inner cannula 102, inflating 404 and deflating 405 the inner cannula first balloon 118 are performed as described above. Once the cavity becomes sufficiently long, the outer cannula 104 is slightly advanced 407. The alternate method, however, continues to return 408 to the advancing 403 of the inner cannula until the entire length of the elongated cavity is dissected to the small diameter of about 7 mm.

Only after the entire length of the elongated cavity has been dissected to the size of the small diameter first balloon 118, does the alternate method perform the step of inflating 409 and deflating 410 the second balloon 122 of the outer cannula to increase the diameter of the distal end of the elongated cavity to about 3 cm. The alternate method then retracts 412 the cannula assembly 100 partially, about the length of the second balloon 122. The alternate method then returns 414 to the steps of inflating 409 and deflating 410 the second balloon 122. The cannula assembly 100 is again retracted 412 partially and the method returns 414 through the above steps until the entire length of the elongated cavity has been enlarged to the diameter of the second balloon 122, about 3 cm.

Another alternate method contemplated by the present invention involves making an incision down to the vessel. Dissection of the vessel from the adjacent tissue is performed for a 3–4 cm length. A blunt tip trocar is placed in the incision, and gas insufflation is initiated.

The vessel dissection cannula is advanced through the blunt tip trocar, and dissection using the small and large diameter balloons is performed under the presence of gas insufflation in the cavity. This technique provides a larger cavity for visualization during the dissection process, since gas insufflation is used from the onset of dissection. However, a gas sealing blunt tip trocar is required. If vessel dissection without gas insufflation is conducted as described in the first technique, and a double rod system is used to maintain the cavity, the use of a blunt tip trocar may be avoided.

Figure 5:
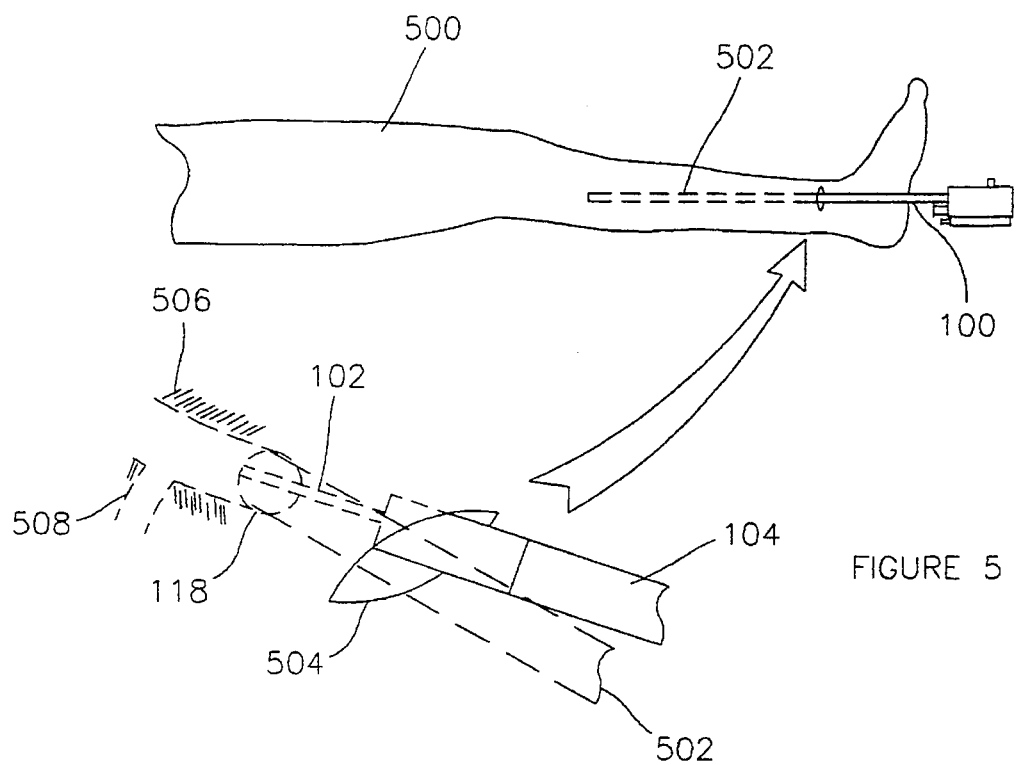
FIG. 5 is an isolated, side view of a patient's leg with the advancement of the cannula assembly through an incision is enlarged.

FIG. 5 illustrates the configuration of the cannula assembly 100 as it is introduced into the leg 500 for saphenous vein 502 dissection. FIG. 5 includes an enlarged view of the inner cannula 102 extending through a skin incision 504 to dissect the tissue 506 surrounding the vein 502 by inflating the first balloon 118. As described above, successive advancement of the inner cannula and repetitive inflation and deflation of the first balloon 118 will move the inner cannula 102 along the course of the vein 502 towards the tributary or side vein 508.

Figure 6:
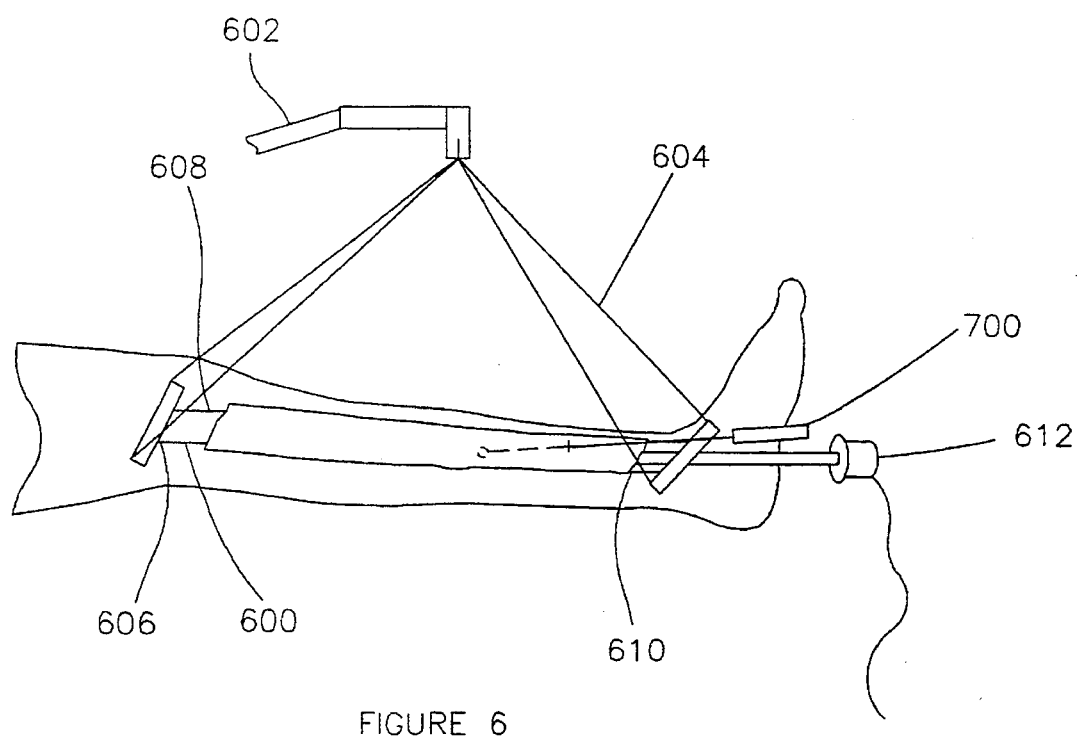
FIG. 6 is an isolated side view of a patient's leg maintaining the elongated cavity with a two rod support system.

Cavity support may be accomplished using a double rod system 600 suspended from a mechanical lifting arm 602 shown in FIG. 6. A suitable mechanical lifting arm 602 is the Laparolift® marketed by Origin Medsystems, Inc. The mechanical lifting arm 602 is connected by cables 604 to end connectors 612 that are attached to two rods like 606 threaded through a proximal 610 and a distal incision 608 along the course of the vessel.

When lifted, the rods 606 support the ceiling of the elongated cavity, and surgical instruments may be introduced into the cavity. The instruments may be introduced through the incisions used for the suspension rods 606, or small incisions may be made in the wall or ceiling of the cavity to allow instrument access.

FIG. 7 depicts an embodiment of a dissection instrument 700 designed to dissect out a vessel 502. It is composed of a rigid open ring 702 attached to a long rigid shaft or handle 704. The ring 702 has an opening 706 through the body of the ring 702. The width of the opening 706 must be at least equal to the diameter of the vessel 502 which is being dissected so that the vessel 502 can pass through the opening 706. The open ring 702 includes at least one cutting edge 708 extending substantially along the circumference of the ring 702. The cutting edge 708 is capable of dissecting tissue and may be curved or twisted out of a single plane generally perpendicular to the handle 704. Preferably, there is a second cutting edge 710 located along the ring's circumference opposite from the first cutting edge 708. This provides dissection in two opposing directions. In operation, the open ring 702 is slipped into position underneath the vessel, and gentle rotational and axial motions are used to free the vessel 502 from adjacent tissue 506.

FIG. 8A depicts the manner in which the position of the dissection instrument 700 is adjusted to allow the open ring 702 to advance down the length of a vessel 502 that contains a side branch 506. The dissection instrument 700 is advanced axially along the vessel 502 to free it from surrounding tissue 506. In 8B, the dissection instrument 700 is rotated to position the opening 706 in the ring towards the takeoff of the side branch 506. Once dissection has proceeded past the side branch 506, the dissection instrument 700 may be rotated back to its initial orientation as illustrated in 8C.

Other dissection instruments may include a probe with an elastomeric distal tip. The tip may be grooved or textured to provide a roughened surface for blunt dissection. A small diameter hook with a connection for electrocautery 612 as seen in FIG. 6 may be used to dissect and cauterize side branches. The side branches like 506 may be cut with scissors at the cauterized sections to allow removal of the dissected vessel 502.

What is claimed is:

1. A dissection device for isolating a vessel from connected tissue along the course of the vessel, the device comprising:

a slotted rigid ring having at least one tissue-dissecting edge extending substantially along the circumference of the ring, the slot in the ring having a width at least equal to the width of the vessel; and an elongated, rigid support member connecting to and extending generally perpendicular to a plane formed by the ring.

2. The device of claim 1, wherein the ring includes a second cutting edge extending along the circumference of the ring opposite said one cutting edge.

3. A dissection device for isolating a vessel partially exposed by an elongated cavity along the course of the vessel, the device comprising:

a slotted rigid ring having at least one cutting edge capable of dissecting tissue, the cutting edge extending substantially along the circumference of the ring in a single plane generally perpendicular to the handle, the ring having a width at least equal to the width of the vessel; and an elongated, rigid handle connected to and extending generally perpendicular to the ring.

4. A dissection device for isolating a vessel from connected tissue along the course of the vessel, the device comprising:

an element forming a substantially ring-like circumference having a slot therein and an open inner region substantially surrounded by the circumference, the slot having a width not substantially smaller than the width of the vessel and the circumference of the element including at least one tissued-dissecting edge extending substantially around the circumference of the element; and an elongated member attached to the element along the circumference thereof and extending therefrom substantially normal to a plane formed by the ring-like element.

5. The dissection device according to claim 4 wherein the elongated member is attached to the element substantially diametrically opposite the slot in the circumference of the element.

6. The dissection device according to claim 4 wherein the element is substantially cylindrical in substantial axial alignment with the elongated member and includes another tissue-dissecting edge thereon disposed substantially about the circumference of the element opposite said one tissue-dissecting edge.

* * * * *